United States Patent [19]

Holtzclaw et al.

[11] Patent Number: 5,005,399
[45] Date of Patent: Apr. 9, 1991

[54] RESISTIVELY HEATED GAS CHROMATOGRAPH SYSTEM

[75] Inventors: James R. Holtzclaw, Palm Harbor; Steven J. Madry; R. Craig Lashley, both of Largo, all of Fla.

[73] Assignee: Brunswick Corporation, Skokie, Ill.

[21] Appl. No.: 394,758

[22] Filed: Aug. 16, 1989

[51] Int. Cl.$^5$ ............................................. G01N 30/02
[52] U.S. Cl. ................................................... 73/23.39
[58] Field of Search ................ 73/23.35, 23.36, 23.39; 55/267, 197, 386; 210/198.2

[56] References Cited

U.S. PATENT DOCUMENTS

| 3,169,389 | 2/1965 | Green, Jr. et al. | 73/23.39 |
| 4,726,822 | 2/1988 | Cates et al. | 55/267 |

FOREIGN PATENT DOCUMENTS 2344838  4/1980  France .

OTHER PUBLICATIONS

*Open Tubular Column Gas Chromatography*, by Milton L. Lee (1984).
"Compact Gas Chromatograph Probe for Gas Chromatography/Mass Spectrometry Utilizing Resistively Heated Aluminum–Clad Capillary Columns", *Analytical Chemistry*, vol. 61, No. 21, Nov. 1, 1989 (pp. 2410-2416).

*Primary Examiner*—Jerry W. Myracle
*Attorney, Agent, or Firm*—Wood, Phillips, Mason, Recktenwald & VanSanten

[57] ABSTRACT

A portable gas chromatograph assembly for detecting chemical species comprises a sample collector/injector for introducing a sample into the system, a cryogenically enhanced stationary phase focusing zone for reducing the band width of the introduced sample, one or more resistively heated conductive film clad, fused silica capillary gas chromatograph columns and associated support structure for separating the sample mixture into its individual components, column temperature control electronics, and a detector for registering the sample components.

12 Claims, 7 Drawing Sheets

RESISTIVELY HEATED GAS CHROMATOGRAPH SYSTEM

FIELD OF THE INVENTION

This invention relates to a gas chromatograph system and, more specifically, to a temperature control therefor.

BACKGROUND OF THE INVENTION

High performance gas chromatographs traditionally have been limited to use in the laboratory because of power, size and weight constraints imposed on field instruments. Further, problems have been associated relative to the use of cryogenic liquids to achieve sample focusing, limited temperature programming rates, and accurate temperature control of the chromatograph column.

The use of directly heated gas chromatograph columns has been previously suggested for a nonoxidizable steel column as shown generally in French Patent No. 2,344,838. Further, direct heating has been suggested for a metal coated fused silica capillary column. In fact, Cates et al U.S. Pat. No. 4,726,822 describes a fast response thermochromatographic capillary column comprising a fused silica capillary with a high temperature chemically inert polymer coating thereon supporting a thin heater film formed by the deposition of either a high resistance metallic compound or a nichrome film sputtered onto the polymer clad capillary tubing. Such a column is directly heated by passing a current through the film. However, this patent does not solve the problem of accurately controlling the temperature, or providing an appropriate low thermal mass support for the resistively heated column.

Gas chromatograph systems have used stationary phase focusing to achieve sample bandwidth narrowing. With more volatile species cryogenic enhancement improves the focusing of the volatile species Cryogenic focusing on short column sections or on whole columns has been known utilizing liquid nitrogen. However, use of liquid nitrogen is not practical on portable units.

The present invention is intended to overcome one or more of the problems as set forth above.

SUMMARY OF THE INVENTION

It is one object of the invention to provide a directly heated gas chromatograph column assembly including control means for directly heating the column.

Broadly, there is disclosed herein a directly heated gas chromatograph column assembly including a fused silica capillary column coated with an electrically conductive film heated by passing an electrical current through the film. A pair of electrical conductors are each connected to the film. An insulating low thermal mass support carries the column. A control means is electrically connected to the conductors for selectively developing a current through the film to directly heat the column.

It is a feature of the invention that the control means determines the temperature of the column and controls the current through the film to maintain the column at a desired temperature.

It is a further feature of the invention that the temperature is determined by sensing resistance of the film.

It is yet another feature of the invention that the resistance is sensed by detecting voltage across the film and current through the film and comparing the detected voltage to the detected current to determine the resistance of the film.

It is a further feature of the invention that the column assembly includes a thick film liquid phase coated on the inside of a portion of the column and means for directly cooling the portion of the column to provide cryogenically enhanced stationary phase focusing.

It is an additional feature of the invention that the cooling means comprises a thermoelectric cooler.

Specifically, there is disclosed herein a miniature, low power, temperature programmable gas chromatograph assembly. The assembly is described incorporating a sample inlet, a cryogenically enhanced stationary phase focusing zone, a resistively heated conductive film clad gas chromatograph column and its supporting structure, column temperature control electronics, and a detector.

Moreover, an apparatus is described for detecting chemical species comprising a sample collector/injector for introducing a sample into the system, a cryogenically enhanced stationary phase focusing zone for reducing the band width of the introduced sample, one or more resistively heated conductive film clad, fused silica capillary gas chromatograph columns and associated support structure for separating the sample mixture into its individual components, column temperature control electronics, and a detector for registering the sample components.

It is another object of the invention to provide a means for heating and cooling a chromatograph column in a gas chromatograph system with a minimum amount of power. Such an object is achieved due to the low thermal mass of the conductive film clad, resistively heated gas chromatograph column, and the insulating properties of the support for the column.

It is another object of the invention to accurately measure and control the temperature of the resistively heated, conductive film coated fused silica capillary column, during isothermal operation as well as during rapid temperature programming Such object is accomplished by directly or indirectly measuring the resistance change of one or more conductive films on the capillary, and by use of the appropriate temperature control circuits and closed loop control algorithms.

It is still a further object of the invention to provide a low power, lightweight apparatus for reducing the band width of the introduced sample which does not require the use of liquid or solid cryogenic materials. This object is achieved by use of a thermoelectrically cooled section of capillary column coated with a thick film liquid phase to achieve cryogenically enhanced stationary phase focusing and a means for rapid heating of the column.

Further features and advantages of the invention will readily be apparent from the specification and from the drawings.

DESCRIPTION OF THE INVENTION

Figure 1:
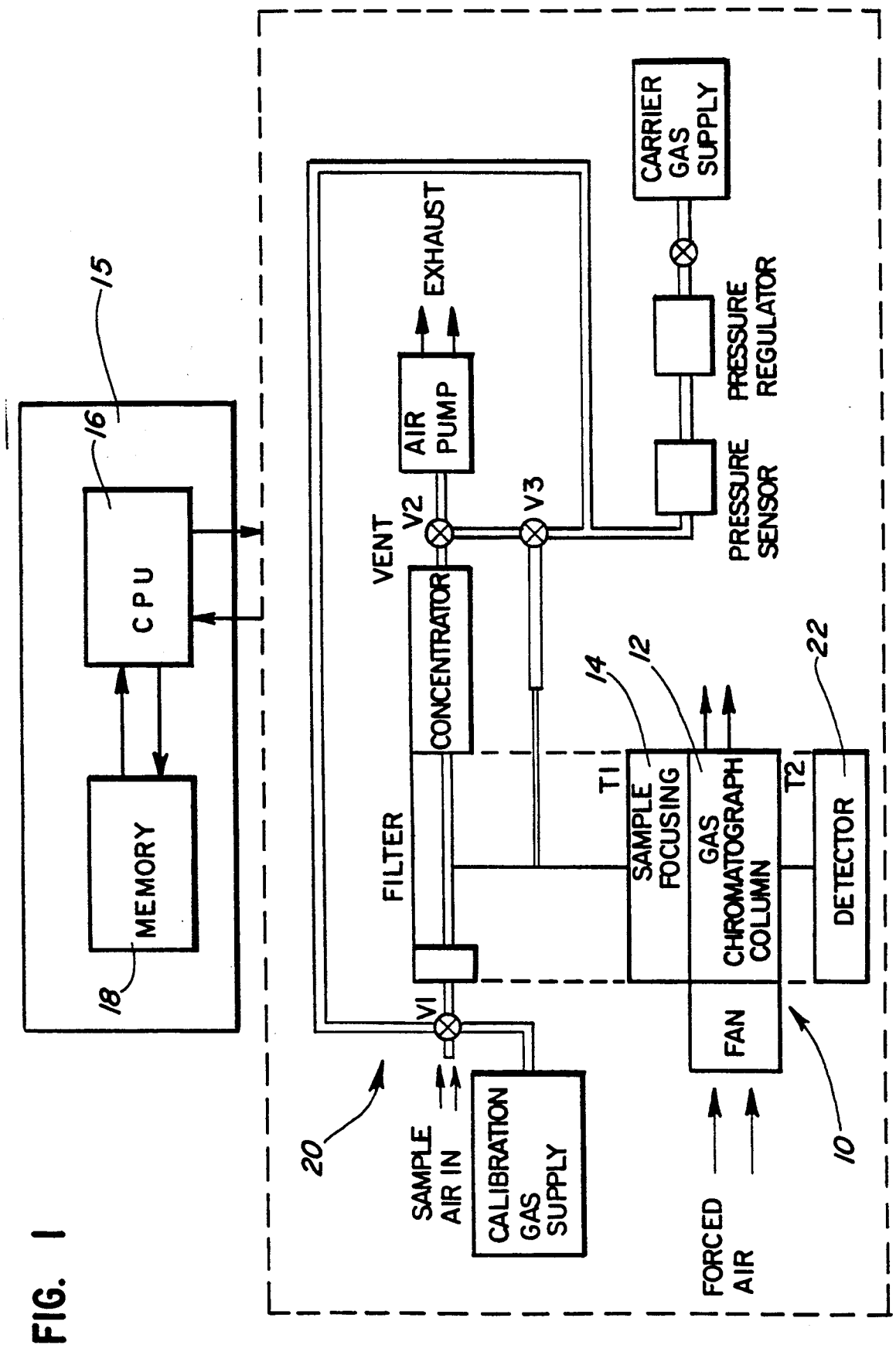
FIG. 1 is a system block diagram illustrating a portable gas chromatograph system suitable for automatic air sampling.

Referring first to FIG. 1, a typical application is illustrated utilizing a gas chromatograph system 10 according to the invention. Specifically, in the illustrated example, the gas chromatograph system 10 according to the invention includes a gas chromatograph assembly 12, a cryogenically enhanced stationary phase focusing zone 14, and controller 15. The controller 15 includes a processor, or CPU, 16 having a connected memory device 18 for storing software for controlling the gas chromatograph system 10.

In the illustrated example, the gas chromatograph system 10 is used in connection with a sample collector/injector 20 for introducing a sample into the system 10. The introduced sample passes through the cryogenically enhanced stationary phase focusing zone 14 for reducing the band width of the introduced sample, through the temperature controlled gas chromatograph column assembly 12 and to a detector 22 for registering the sample components.

The sample collector/injector system 20 does not form part of the invention and is illustrated by way of example only. Other configurations employing the gas chromatograph system 10 are possible. Such alternate configurations include gas chromatograph system incorporating inlets configured for syringe injection of the sample; gas chromatograph systems incorporating inlets configured for purge and trap or head space analysis; gas chromatograph systems adapted for accepting pyrolysis products; and gas chromatographs configured for the use of auto samplers, as are conventional and well known.

Figure 2:
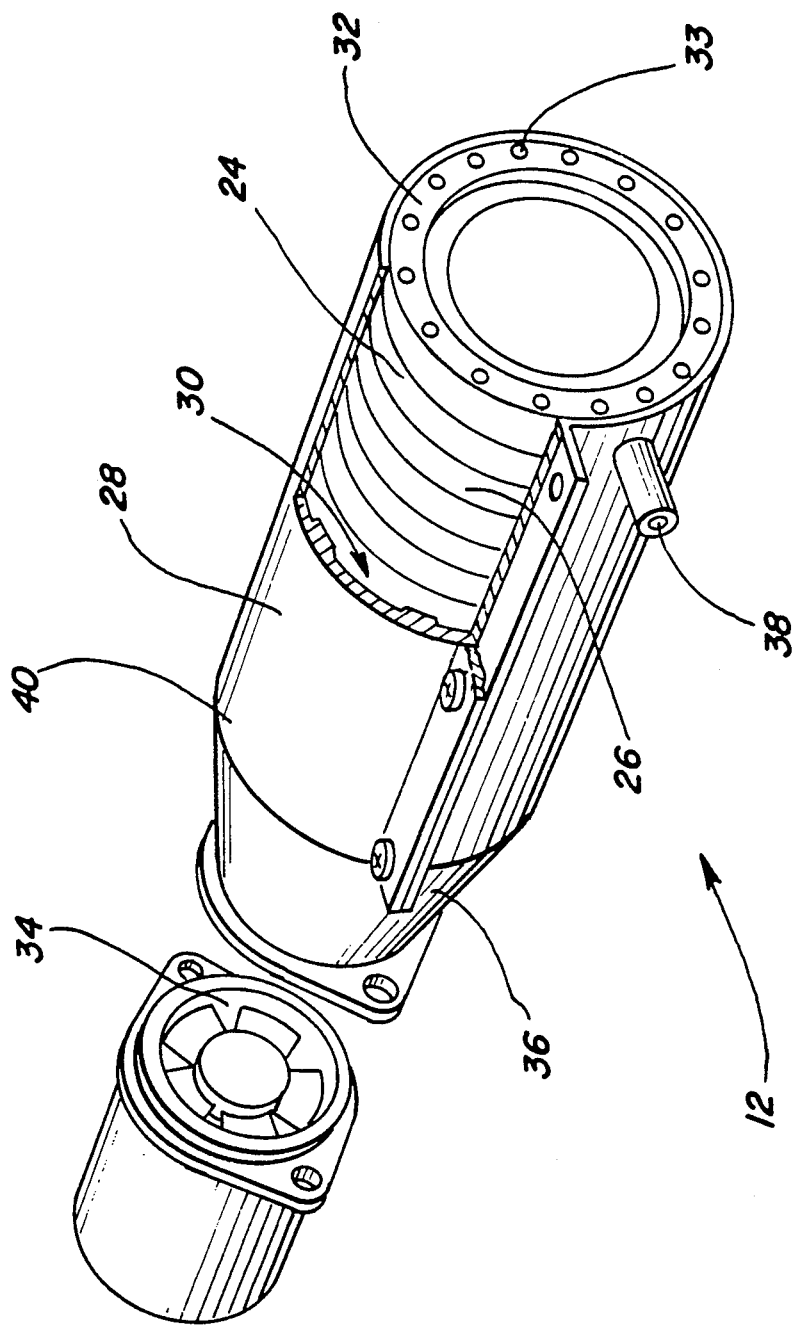
FIG. 2 is a perspective view of a gas chromatograph assembly according to the present invention.

Referring now to FIG. 2, the gas chromatograph assembly 12 comprises a column 24 wound on an insulating mandrel 26. The mandrel 26 is covered by a close fitting shell, or outer shield, 28 to define an air gap 30 therebetween. The air gap 30 at each end of the assembly is covered by a baffle, one of which is illustrated at 32, including apertures 33. Thus, a still air gap 30 is created between the column 24 wound on the mandrel 26 and the outer close fitting shell 28. This air gap ensures good thermal insulation and if the spacing of the gap 30 is correctly chosen, eliminates heat losses due to thermal convection. In the proper configuration, the only significant heat losses are conductive heat loss through the insulating mandrel 26 and radiative heat loss through the still air gap 30.

The resistively heated gas chromatograph column 24 consists of a conductive film coated fused silica column, coated with a protective electrically insulated film. The film is connected to electrical conductors 38 and 40 for applying power to each end of the column 24. Such a column 24 may be similar to that described in Cates et al. U.S. Pat. No. 4,726,822, the specification of which is hereby incorporated by reference herein. The use of any conductive film for the column 24 is suitable. More than one conductive coating/insulating film combination can be used.

A cooling fan 34 is connected through an air flow spreader 36 at one end outwardly of the baffle 32. The fan 34 is utilized to force cool air through the baffles 32 and air gap 30 to allow rapid cooling of the column 24 as necessary, or desired.

The conductive film coated column 24 is supported by the mandrel 26 in such a manner as to maintain uniform heating both longitudinally and radially with respect to the column 24, to minimize the thermal mass of the gas chromatograph column assembly 12, to minimize convective and conductive heat losses, and to permit rapid heating and cooling of the column from time to time Therefore, the power required to heat and cool the gas chromatograph column 24 is minimized due to the extremely low thermal mass of the column assembly 12 and the insulating properties of the column assembly 12.

Alternative configurations not disclosed herein include wrapping the resistively heated column on a conventional capillary column cage or other low thermal mass support and enclosing the resulting assembly in a suitable insulating enclosure. As a further alternative, the resistively heated column may be embedded in an insulating material for isothermal operation.

Figure 4A:
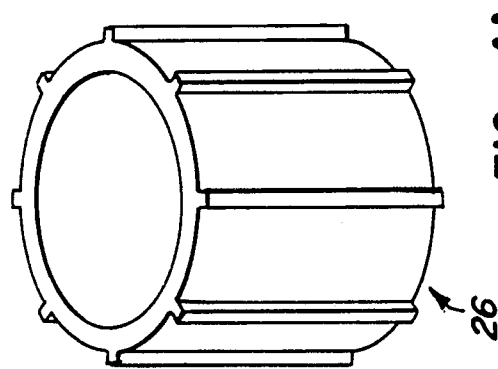
FIGS. 4A-4C illustrate a perspective view, a plan view, and an elevational view with a portion magnified, respectively, for the column support of FIG. 3.
Figure 4B:
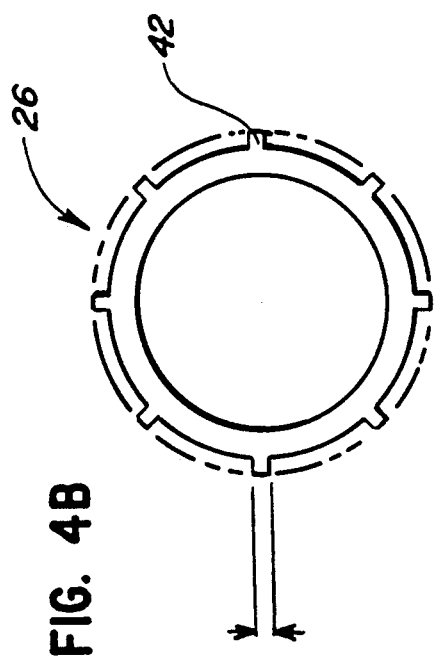
Figure 4C:
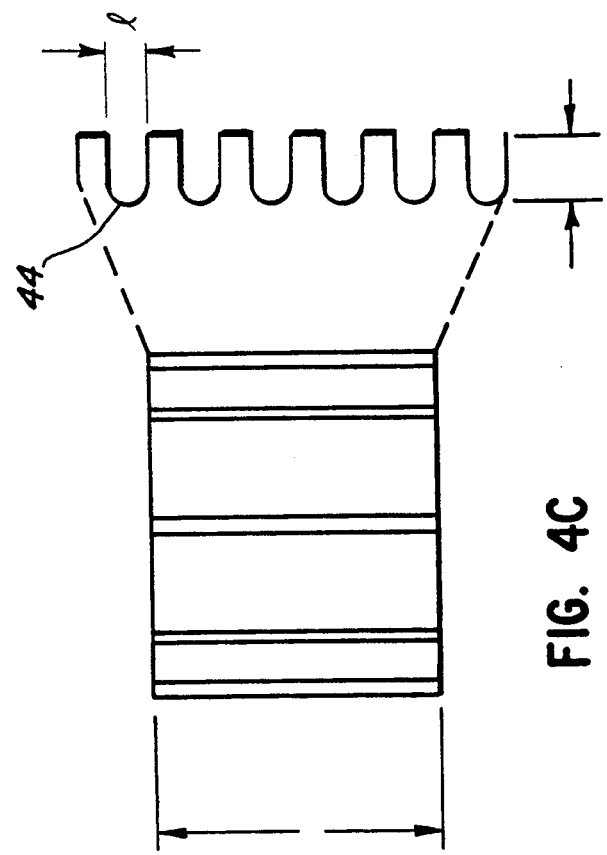

Referring also to FIGS. 4A-4C, the mandrel 26 is generally cylindrical and includes eight outwardly extending and equally circumferentially spaced supports 42. As is specifically illustrated in FIG. 4C, each support 42 includes a plurality of longitudinally spaced notches 44 of a size l for receiving the column 24. Accordingly, the column 24 is spirally wound around the mandrel 26 and is supported in the notches 44.

Figure 3:
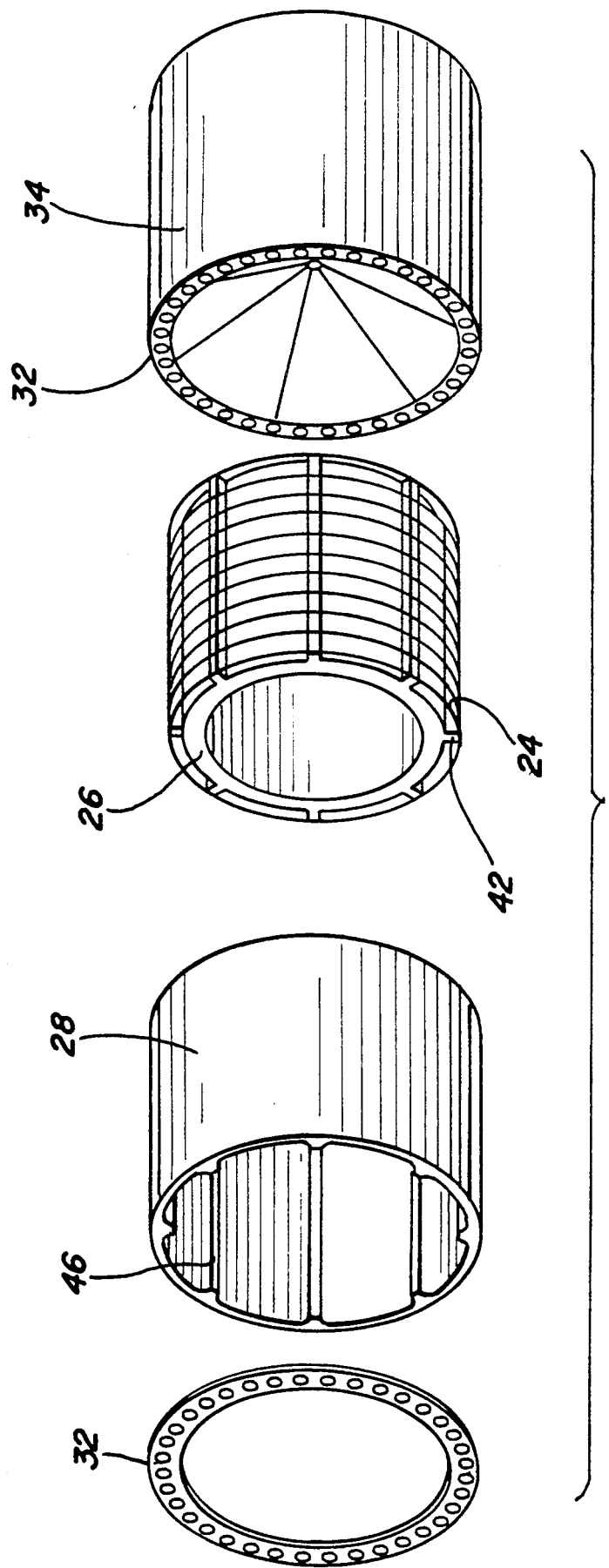
FIG. 3 is an exploded view of the gas chromatograph assembly of FIG. 2.

As is also shown in FIG. 3, the cover shell 28 is generally cylindrical and includes a plurality of radially inward extending supports 46, one for each of the mandrel supports 42. In fact, when the cover 28 is placed over the mandrel 26, the cover supports 46 are aligned and abut the mandrel supports 42 to ensure that the column 24 is retained within the notches 44.

Although the mandrel 26 and shell 28 may be formed of various different materials, teflon has been found to be a suitable material for construction of both due to its properties as a low thermal mass.

In the illustrated embodiment, the gas chromatograph system 10 utilizes a miniature, portable, low power gas chromatagraph assembly 12. In fact, a column 24 15 meters in length, and having an outer diameter on the order of 0.485 millimeters can be wound on a mandrel 26 which is 2.5 inches in length.

Figure 5:
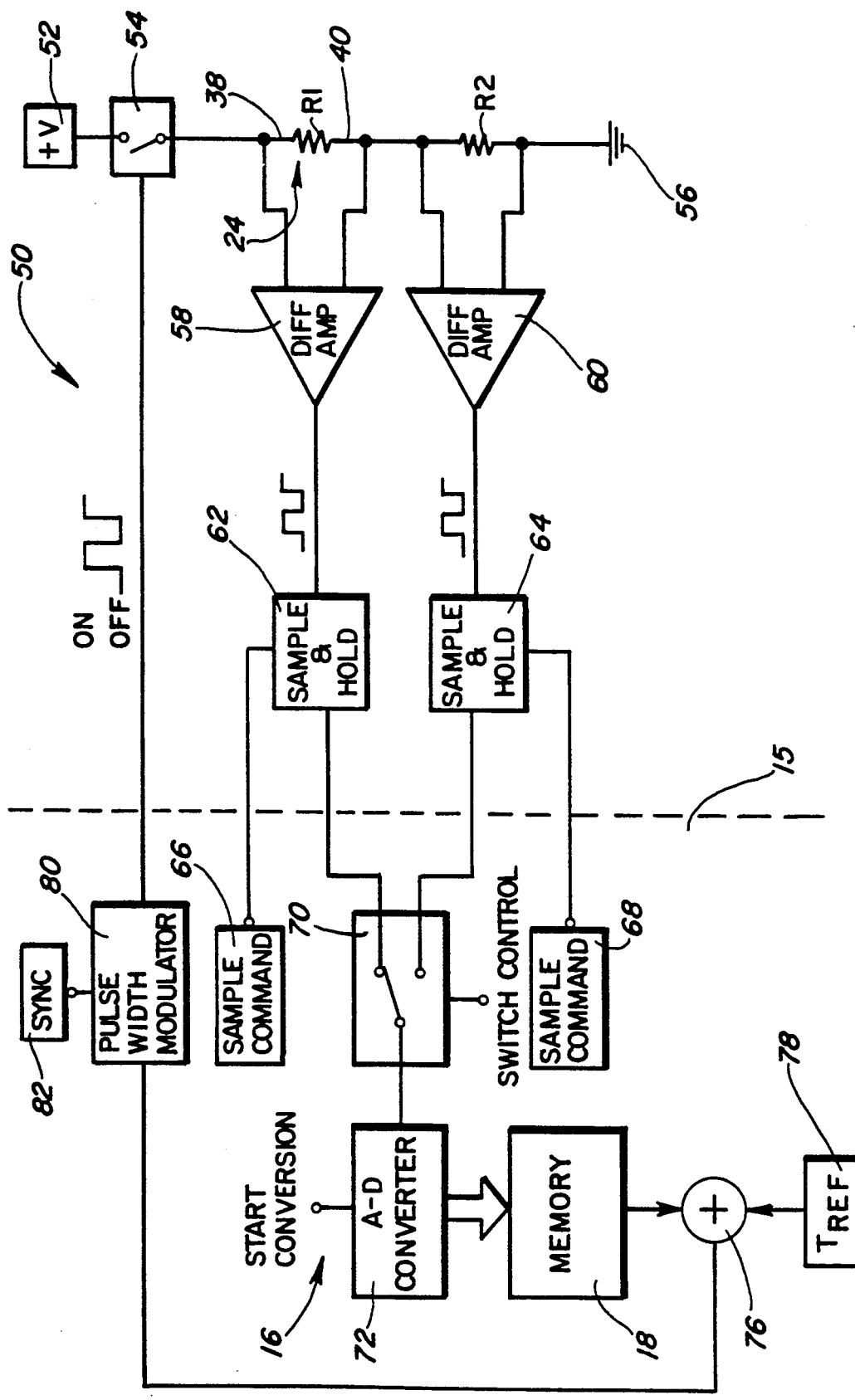
FIG. 5 comprises a block diagram representing a control according to the invention for the gas chromatograph assembly of FIG. 2.

With reference to FIG. 5, a block diagram of a software program illustrates a temperature control 50 for the gas chromatograph assembly 12.

Particularly, as is well known, the resistance of a conductor increases with increases in conductor temperature. Therefore, by directly or indirectly measuring the resistance of the metal coating and relating it to column temperature through the use of the resistance temperature coefficient of the particular conductive film, temperature can be effectively controlled. The function of the temperature control circuit 50 is to control the temperature of the gas chromatograph column 24, see FIG. 2. The execution of this control function requires that the control circuit 50 vary the voltage applied across the conductive film clad column 24, and thus the current therethrough, and to determine the temperature of the column 24.

The film layer for the column 24 is illustrated as a resistor R1 in FIG. 5 connected between the conductors 38 and 40. A voltage source 52 is connected through a switch 54 in series with the resistor R1 and a precision resistor R2 to ground, indicated generally at 56. Although the switch 54 could be any known type switch, a switching transistor has been found to be acceptable due to its switching speed. In accordance with the above circuit, the temperature of the column 24 can be rapidly increased by closing the contact of the switch 54 to couple the power source 52 to the resistor R1. Rapid cooling is provided upon deenergization of the switch 54 owing to the low thermal mass, as discussed above.

In order to sense resistance of the column 24, a first differential amplifier 58 is connected across the effective resistance of the column, as represented by the resistor R1, to determine the voltage across the resistor R1. A second differential amplifier 60 is used to measure the voltage developed across the precision resistor R2. The voltage developed across the precision resistor R2 is proportional to the current through the column since the current sensing resistor R2 is in series with the column resistor R1. Therefore, since both the voltage across the column, as determined by the first differential amplifier 58, and a voltage proportional to the current through the column, as determined by the second differential amplifier 60, are known, the resistance of the column can be determined using ohms law by dividing the column voltage by the column current, as is well known.

The differential amplifiers 58 and 60 are connected to the controller 15 through sample and hold circuits 62 and 64, respectively. Specifically, a sample command from respective blocks 66 and 68 are transmitted to respective sample and hold circuits 62 and 64 each time the switch 54 is closed. The controller through a switch control circuit 70 switches the output of the sample and hold circuits 62 and 64 into an A-D converter 72 which then stores a digital representation of the voltage and current in the memory device 18.

The temperature value stored in the memory 74 is transferred to a summer 76 which also receives a temperature reference value from a set point block 78. Specifically, the temperature reference value represents a programmable desired column temperature which may be determined in any known or conventional manner. The output of the summer 76 is a temperature error which is applied to a pulse width modulator 80. The temperature error represents the difference between the actual temperature from the memory circuit 74 and the reference or set point temperature from the block 78.

The pulse width modulator 80 receives a synchronization signal from a block 82. The pulse width modulator 80 is operable to output a pulse control signal to the switch 54. The control signal comprises a pulse train having a frequency determined by the synchronization circuit 82 and a duty cycle corresponding to the temperature error. Specifically, if the sensed temperature is below the reference temperature, then the duty cycle is increased so that the voltage is applied across the resistor R1 for a greater length of time. Conversely, if the sensed temperature it too high, then the duty cycle is decreased so that a rapid temperature drop is effected.

A requirement of the temperature control circuit is to maintain the actual column temperature relative to ambient within plus or minus 1° C. of the desired temperature. Since the operation of the control circuit 50 requires rapid column temperature ramp rates, the capacity of the heater and the dynamic response of the control circuit 50 must be sufficient so that the actual temperature does not lag more than 1° behind the desired temperature and does not overshoot the desired temperature by more than one degree when the ramp stops.

Figure 6:
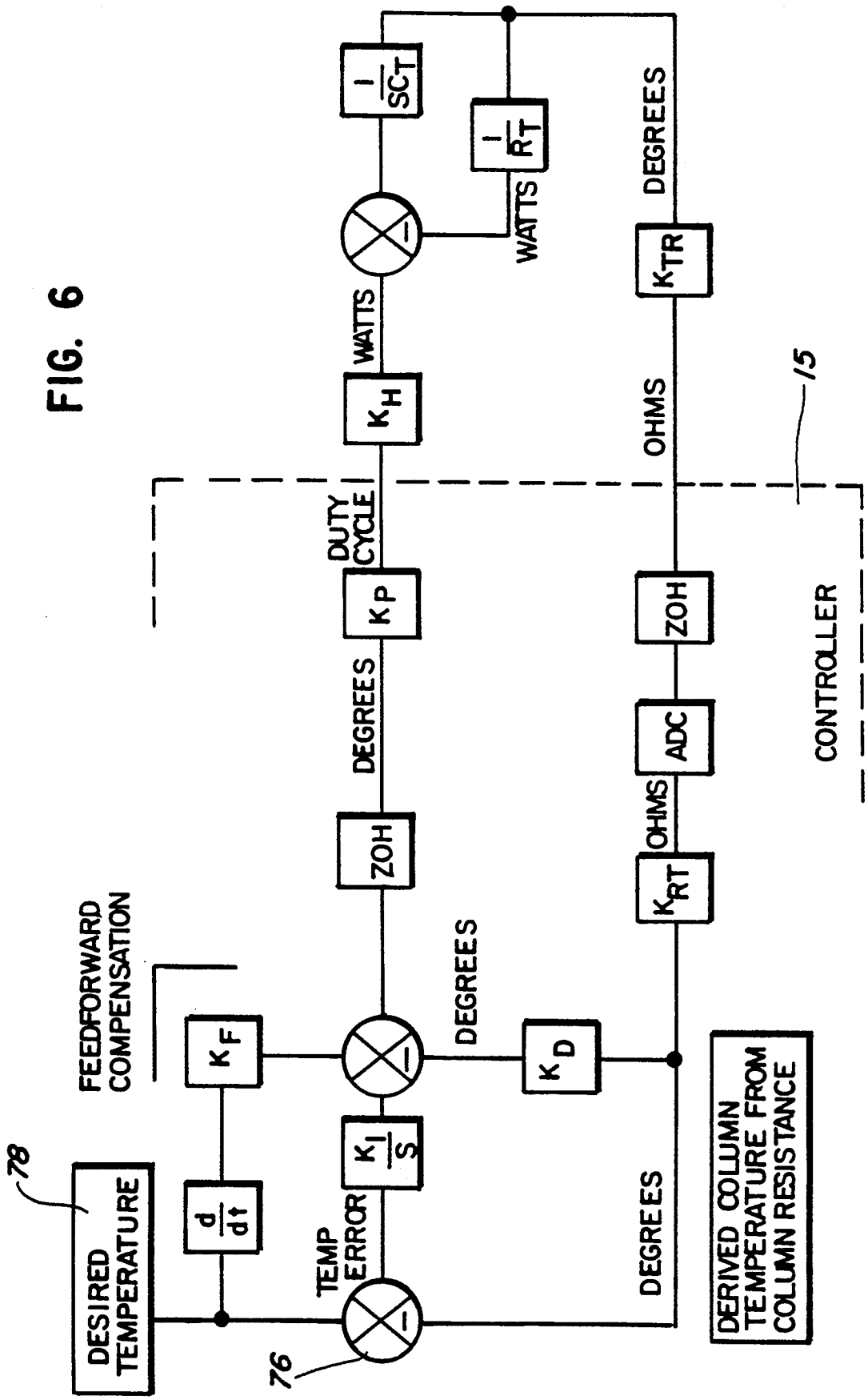
FIG. 6 comprises a transfer function block diagram of the control of FIG. 5.

FIG. 6 illustrates a transfer function block diagram of a closed loop temperature control system detailing the manner of temperature control and defining the sources of error. Table 1 listed below contains definitions of the symbols used in FIG. 6.

TABLE 1

KEY TO SYMBOLS IN FIG. 6

$K_F$—Feedforward Compensation Gain (degree/s / degree/s)

$K_I$—Integral Compensation Gain (degrees/degree)

ZOH—Zero Order Hold [$1/(1+ST/2)$ where T is sampling rate in s]

$K_P$—Pulse Width Modulator Gain (duty cycle/degree)

$K_H$—Heater Gain (watts/duty cycle)

$C_T$—Thermal Capacitance of GC Column (watts/degree)

$R_T$—Thermal Resistance of GC Column (degrees/watt)

$K_{TR}$—Thermal Characterization of GC Column (ohms/degree)

ADC—Analog-Digital Converter Gain (volts/volt)

$K_{RT}$—Thermal Characterization of GC Column (degrees/ohm)

$K_D$—Pseudo-Derivative Feedback Gain (degrees/degree)

The actual column temperature relative to ambient is derived by exploiting the changes that occur in the resistivity of the conductive film column coating as a function of temperature. The control loop measures the resistance of the conductive film heating element, represented by R1 in FIG. 5, and uses a look-up table in the memory 18 of the controller 15 to convert the measured resistance into an equivalent temperature. This look-up table is a thermal characterization of the column and relates the resistance of the column to its temperature. This temperature is compared with the desired temperature. Any temperature error is dynamically compensated and applied to the pulse width modulater 80, see FIG. 5, which increases the temperature of the GC column 24. It is imperative that the control loop does not allow significant temperature overshoot since no active cooling element will be used in the temperature controller to correct such overshoots. This constraint requires a well-damped response on the part of the control loop to commanded temperature changes.

Alternatively, the column control could be based solely on the measured resistance of the conductive film clad column without the need to refer to a look-up table.

The design of the GC column temperature controller and compensation network is in the discrete domain. However, because there is more familiarity with continuous systems (i.e., analog control loops) than with discrete systems (i.e., digital control loops), a better intuitive understanding of the operation of the temperature controller is obtained if the discrete control loop is represented as a continuous system. Since the control loop can be represented by continuous transfer functions, it is therefore possible to control the temperature of the GC column 24 entirely with analog circuitry.

It is apparent from FIG. 6 that the capacity of the heater must be sufficient to overcome the effects of the thermal resistance and still be able to change the temperature of the thermal mass at the desired rate. Assuming that the heater has this capacity, the bandwidth of the control loop must be sufficiently high and the control loop must have sufficient damping to follow the variations in the desired temperature without the temperature lag or the temperature overshoot exceeding the temperature controller specifications.

The stability of the control loop, a well-damped small signal transient response, the ability to follow ramping inputs, and the rejection of temperature disturbances are achieved with the inclusion of pseudo-derivative feedback and integral forward gain This configuration—with proper gain selection of other loop elements—allows high phase margin (good damping) and the classic $-20$ dB/decade slope of the open loop gain at the unity gain open loop frequency. The inclusion of the integral gain term increases the system type to a Type 1 system; therefore, for a constant input there is zero temperature error and for a ramping input there is a fixed error, the steady state value of which is determined by the gain selection of other loop elements.

Feedforward compensation is employed to improve the transient performance of the temperature controller. Since the feedforward compensation is not part of the closed loop, its effect is not encumbered by the closed loop response of the controller, and its inclusion does not affect the stability of the system. The use of feedforward compensation decreases the initial temperature lag and improve the dynamic response to time varying inputs.

CRYOGENICALLY ENHANCED STATIONARY PHASE FOCUSING

The ability to reproducibly inject a narrow slug of sample onto the front end of the column 24 is essential for good chromatographic resolution. The sample injection is even more critical when the sample is thermally desorbed from a sorbent into a volume of carrier gas. In order to achieve a "slug-like" injection, the sample bandwidth needs to be narrowed. This process can be achieved by stationary phase focusing.

In gas chromatography, the distribution constant, $K_D$ is related to the phase ratio, $\beta$, by the partition ratio or capacity factor k', through the following relationship:

$$K_D = \beta K'$$

k' determines the velocity of the solute band as it passes down the chromatographic column 24. The importance of this relationship to sample focusing is whether all the molecules in the sample band are traveling at the same rate or, in other words, have the same k'. For example, if the molecules in the rear of the sample band have a smaller k', then the sample band will be narrowed or "focused". The above relationship can be expanded to:

$$C_L/C_G = (V_G/V_L)k'$$

where $C_L$ and $C_G$ represent solute concentrations in the stationary (liquid) and mobile (gas) phases, respectively; $V_G$ and $V_L$ represent the volume of column occupied by mobile (gas) and stationary (liquid) phases, respectively; and k' is the partition ratio (capacity factor) of the solute. Therefore, by changing $C_L$, $C_G$, $V_G$, or $V_L$, the sample bandwidth can be changed.

In stationary phase focusing, sample bandwidth narrowing is achieved in the following manner. As the sample enters the stationary phase focusing column, the front of the sample band encounters the column liquid phase and dissolves into it. Consequently, $C_L/C_G$ increases, and as shown by the above equation, the k' at the front of the sample band is increased. This means that the front of the band moves more slowly than the rear and the sample band is narrowed. Once the entire sample has been transferred onto the column, the focusing column can be rapidly heated and the narrowed sample flashed onto the chromatograph column.

Stationary phase focusing provides the required sample bandwidth narrowing for the less volatile solvent vapors. However, it may be difficult to efficiently focus very volatile species. Cryogenic enhancement can be used to improve the focusing of volatile species. The theory for the cryogenic focusing effect is identical to that for stationary phase focusing. As the sample band moves into a cryogenically cooled section of column, the front of the sample band encounters a colder environment than does the rear of the band. In the colder environment, $C_L/C_G$ increases. Consequently, as discussed above, the front of the band moves more slowly than the rear and the sample band is narrowed.

Cryogenic focusing on a very narrow section of column has been employed by cooling a section of the column with liquid nitrogen. Unfortunately, cryogenic cooling to liquid nitrogen temperatures is impractical for small gas chromatographs due to size, weight, and power constrains and the need to minimize consumables. Consequently, an approach is needed that permits cryogenic focusing to take place at a higher temperature.

It is known that utilizing a column coated with a thick film liquid phase greatly improves the efficiency of the cryofocusing process. It is possible to use cryogenically enhanced, stationary phase focusing at a temperature between $-40°$ to $0°$ C. using a film thickness of 3.0 $\mu$m or greater on a section of capillary column.

According to the invention herein, this temperature range can be easily achieved with a miniature thermoelectric cooler. Consequently, a cryogenically enhanced stationary phase focusing apparatus can consist of a section of capillary tubing coated with a thick film liquid phase and in thermal contact with a thermoelectric cooler. An additional means for rapid heating of the cooler may be provided.

Figure 7:
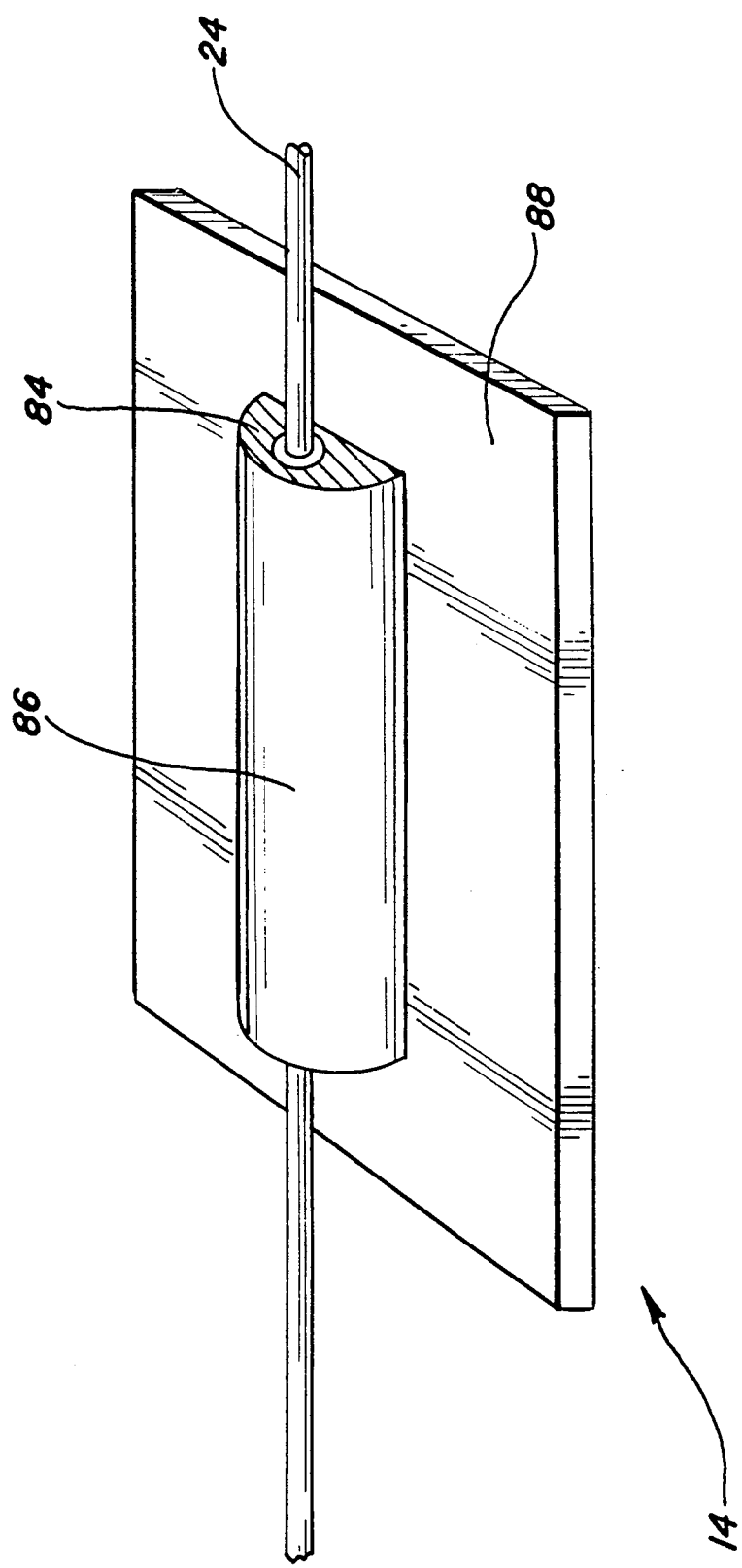
FIG. 7 illustrates in perspective view an implementation for achieving cryogenically enhanced stationary phase focusing according to the invention.

Referring to FIG. 7, an illustrated example of the cryogenically enhanced stationary phase focusing zone 14, see FIG. 1, is illustrated. Particularly, a portion of the column 24 includes a thick film liquid phase coated on the inside. This liquid phase may comprise, for example, a silicon oil chemically bonded to a portion of the inside of the column 24. A conventional thermoelectric cooler 84, having sealed ends, is provided surrounding the portion of the column 24. A hollow, thermally conductive shell 86 is bonded in thermal contact with the cooler 84, and is secured to a thermoelectric heat sink 88. As is well known, the thermoelectric cooler 84 is operable to absorb heat when current is sent through the cooler.

Thus, the invention broadly comprehends an apparatus for detecting chemical species comprising a sample collection/introduction inlet, a cryogenically enhanced stationary phase focusing region, a resistively heated gas chromatograph column, a detector, and a temperature control.

We claim:

1. A directly heated gas chromatograph column assembly comprising:
    a fused capillary column coated with an electrically conductive film heated by passing an electrical current through said film;
    a pair of electrical conductors each connected to said film;
    an insulating low thermal mass support carrying said column for minimizing heat loss and permitting rapid heating and cooling of said column; and
    control means electrically connected to said conductors for selectively developing a current through said film to directly heat said column.

2. The column assembly of claim 1 wherein said control means comprises means for determining the temperature of said column and means for controlling the current through said film to maintain the column at a desired temperature.

3. A directly heated gas chromatograph column assembly comprising:
    a fused silica capillary column coated with an electrically conductive film heated by passing an electrical current through said film;
    a pair of electrical conductors each connected to said film;
    an insulating low thermal mass support carrying said column; and
    control means electrically connected to said conductors for selectively developing a current through said film to directly heat said column, said control means comprises means for determining the temperature of said column and means for controlling the current through said film to maintain the column at a desired temperature, said determining means comprises means for sensing resistance of said film.

4. The column assembly of claim 3 wherein said sensing means includes first means for detecting voltage across said film, second means for detecting current through said film and means for comparing the detected voltage to the detected current to determine the resistance of said film.

5. A directly heated gas chromatograph column assembly comprising:
    a fused silica capillary column coated with an electrically conductive film heated by passing an electrical current through said film;
    a pair of electrical conductors each connected to said film;
    an insulating low thermal mass support carrying said column;
    control means electrically connected to said conductors for selectively developing a current through said film to directly heat said column; and
    a thick film liquid phase coated on the inside of a portion of said column and means for directly cooling said portion of the column to provide cryogenically enhanced stationary phase focusing.

6. The column assembly of claim 5 wherein said cooling means comprises a thermoelectric cooler.

7. In a gas chromatograph column assembly including a fused silica capillary column coated with at least one layer of an electrically conductive film heated by means of an electrical current passing through said film, a temperature control comprising:
    means for determining the temperature of said column, said determining means comprises means for sensing resistance to said film; and
    means for controlling the current through said film to maintain the column at a desired temperature.

8. The temperature control of claim 7 wherein said sensing means includes means for detecting voltage across said film, means for detecting current through said film and means for comparing the detected voltage to the detected current to determine the resistance of said film.

9. In a gas chromatograph column assembly including a fused silica capillary column coated with at least one layer of an electrically conducted film heated by means of an electrical current passing through said film a temperature control comprising;
    a means for determining the temperature of said column; and
    means for controlling temperature through said film to maintain the column at a desired temperature, said controlling means comprises a pulse width modulating controller having a duty cycle which is controlled to maintain the column at the desired temperature.

10. A cryogenically enhanced stationary phase focusing apparatus comprising:
    a fused silica capillary column coated with at least one layer of an electrically conductive film heated by means of an electrical current passing through said film;
    a thick film liquid phase coated on the inside of a portion of said column; and
    a thermoelectric cooling device in heat transfer relation with the portion of said column for directly cooling said portion of the column.

11. An apparatus for detecting chemical species comprising:
    a sample inlet;
    a fused silica capillary column coupled with said inlet and being coated with an electrically conductive film heated by passing an electrical current through said film;
    a pair of electrical conductors each connected to said film;
    an insulating low thermal mass support carrying said column;
    means for determining the temperature of said column; and
    means for controlling the current through said film to maintain the column at a desired temperature.

12. An apparatus for detecting chemical species comprising:
    a sample inlet;
    a fused silica capillary column coupled with said inlet and being coated with an electrically conductive film heated by passing an electrical current through said film;
    a pair of electrical conductors each connected to said film;
    an insulating low thermal mass support carrying said column;
    means for controlling the current through said film to maintain the column at a desired temperature;
    a thick film liquid phase coated on the inside of a portion of said column; and
    a thermoelectric cooling device in heat transfer relation with the portion of said column for directly cooling said portion of the column to provide a cryogenically enhanced sample focusing region.

* * * * *